(12) United States Patent
Lu et al.

(10) Patent No.: US 11,260,032 B2
(45) Date of Patent: Mar. 1, 2022

(54) METHOD FOR PREPARING BIOFILM-COATED DRUG NANOCRYSTAL AND APPLICATION THEREOF

(71) Applicant: Shanghai Whittlong Pharmaceutical Institute, Shanghai (CN)

(72) Inventors: Weiyue Lu, Shanghai (CN); Zhilan Chai, Shanghai (CN); Xuefeng Hu, Shanghai (CN); Cao Xie, Shanghai (CN); Huimin Hou, Shanghai (CN); Hao Wang, Shanghai (CN)

(73) Assignee: Shanghai Whittlong Pharmaceutical Institute, Shanghai (CN)

( * ) Notice: Subject to any disclaimer, the term of this patent is extended or adjusted under 35 U.S.C. 154(b) by 0 days.

(21) Appl. No.: 16/499,330

(22) PCT Filed: Mar. 30, 2018

(86) PCT No.: PCT/CN2018/081364
§ 371 (c)(1),
(2) Date: Nov. 10, 2019

(87) PCT Pub. No.: WO2018/177420
PCT Pub. Date: Oct. 4, 2018

(65) Prior Publication Data
US 2020/0069601 A1    Mar. 5, 2020

(30) Foreign Application Priority Data
Mar. 31, 2017    (CN) .......................... 201710207275.6

(51) Int. Cl.
*A61K 9/51*    (2006.01)
*A61K 9/127*    (2006.01)
(Continued)

(52) U.S. Cl.
CPC ............ *A61K 9/5176* (2013.01); *A61K 9/127* (2013.01); *A61K 31/337* (2013.01); *A61K 31/437* (2013.01); *Y10S 977/773* (2013.01)

(58) Field of Classification Search
CPC ..... A61K 9/5176; A61K 9/1271; A61K 9/127
See application file for complete search history.

(56) References Cited

U.S. PATENT DOCUMENTS

2013/0150312 A1* 6/2013 Brown ................ A61K 31/522
    514/23
2013/0337066 A1* 12/2013 Zhang .................... A61P 31/04
    424/489

FOREIGN PATENT DOCUMENTS

CN    103857387 A    6/2014
CN    105456228 A    4/2016
(Continued)

OTHER PUBLICATIONS

Xiaoqing Ren, Rui Zheng, Xiaoling Fang, Xiaofei Wang, Xiaoyan Zhang, Wuli Yang, Xianyi Sha. "Red blood cell membrane camouflaged magnetic nanoclusters for imaging-guided photothermal therapy." Biomaterials, vol. 92, 2016, pp. 13-24, available online Mar. 19, 2016. (Year: 2016).*

(Continued)

*Primary Examiner* — Isaac Shomer
(74) *Attorney, Agent, or Firm* — Bayramoglu Law Offices LLC (57) ABSTRACT

A nano drug delivery system includes a biofilm-coated drug nanocrystal. A drug in a physical form of nanocrystal is directly used as a rigid supporting skeleton, and is filled in a biofilm. The nano drug delivery system has the advantages of high drug loading capacity, good biocompatibility, long systemic circulation time and drug sustained release.

3 Claims, 8 Drawing Sheets
Specification includes a Sequence Listing.

(51) Int. Cl.
  *A61K 31/337* (2006.01)
  *A61K 31/437* (2006.01)

(56) References Cited

FOREIGN PATENT DOCUMENTS

CN 106456551 A 2/2017
WO WO-2016109306 A1 * 7/2016 ........... A61K 9/0019

OTHER PUBLICATIONS

Praveen K. Dubey, Vivek Mishra, Sanyog Jain, Sunil Mahorand S.P. Vyas. "Liposomes Modified with Cyclic RGD Peptide for Tumor Targeting." Journal of Drug Targeting, vol. 12(5), Jun. 2004, pp. 257-264. (Year: 2004).*

Lang Rao et al. "Red Blood Cell Membrane as a Biomimetic Nanocoating for Prolonged Circulation Time and Reduced Accelerated Blood Clearance." Small, vol. 11 No. 46, 2015, pp. 6225-6236. (Year: 2015).*

N. Nakagiri, M.H. Manghnani, L.C. Ming, and S. Kimura. "Crystal Structure of Magnetite under Pressure." Physical Chemistry of Minerals, vol. 13, 1986, pp. 238-244. (Year: 1986).*

Yi-fei Zhang, Jian-cheng Wang, Dong-yan Bian, Xuan Zhang, Qiang Zhang. "Targeted delivery of RGD-modified liposomes encapsulating both combretastatin A-4 and doxorubicin for tumor therapy: In vitro and in vivo studies." European Journal of Pharmaceutics and Biopharmaceutics, vol. 74 (2010), 467-473. (Year: 2010).*

Zhilan Chai et al. "facile approach to functionalizing cell membrane-coated nanoparticles with neurotoxin-derived peptide for brain-targeted drug delivery." Journal of Controlled Release 264 (2017) 102-111. (Year: 2017).*

Weiwei Gao and Liangfang Zhang. "Coating nanoparticles with cell membranes for targeted drug delivery." Journal of Drug Targeting, vol. 23(7-8), 2015, pp. 619-626. (Year: 2015).*

Y. Schilt, T. Berman, X.Wei, Y. Barenholz, U. Raviv. "Using solution X-ray scattering to determine the high-resolution structure and morphology of PEGylated liposomal doxorubicin nanodrugs." Biochimica et Biophysica Acta 1860 (2016), pp. 108-119. (Year: 2016).*

Tang Li, David Cipolla, Thomas Rades, Ben J. Boyd. "Drug nanocrystallisation within liposomes." Journal of Controlled Release 288 (2018), pp. 96-110. (Year: 2018).*

Xingong Li et al. "Doxorubicin physical state in solution and inside liposomes loaded via a pH gradient." Biochimica et Biophysica Acta 1415 (1998), pp. 23-40. (Year: 1998).*

Santosh Aryal, Che-Ming J Hu, Ronnie H Fang, Diana Dehaini, Cody Carpenter, Dong-Er Zhang, & Liangfang Zhang. "Erythrocyte membrane-cloaked polymeric nanoparticles for controlled drug loading and release." Nanomedicine (2013), vol. 8(8), pp. 1271-1280. (Year: 2013).*

Rao L. et al. Red Blood Cell Membrane as a Biomimetic Nanocoating for Prolonged Circulation Time and Reduced Accelerated Blood Clearance. Small. Dec. 31, 2016, 11(46), pp. 1-12.

* cited by examiner

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: Polypeptide A7R with a high binding activity to
      both vascular endothelial growth factor receptor-2 and neuropilin-
      1.

<400> SEQUENCE: 1

Ala Thr Trp Leu Pro Pro Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Polypeptide A7R with a high binding activity to
      both vascular endothelial growth factor receptor-2 and neuropilin-
      1.
<220> FEATURE:
<221> NAME/KEY: misc_feature
<222> LOCATION: (1)..(8)
<223> OTHER INFORMATION: Amino acid is D-amino acid

<400> SEQUENCE: 2

Arg Pro Pro Leu Trp Thr Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Polypeptide A7R with a high binding activity to
      both vascular endothelial growth factor receptor-2 and neuropilin-
      1.
<220> FEATURE:
<221> NAME/KEY: misc_feature
<222> LOCATION: (1)..(8)
<223> OTHER INFORMATION: cyclic polypeptide

<400> SEQUENCE: 3

Cys Ala Thr Trp Leu Pro Pro Arg
1               5

<210> SEQ ID NO 4
<211> LENGTH: 16
<212> TYPE: PRT
<213> ORGANISM: Artificial Sequence
<220> FEATURE:
<223> OTHER INFORMATION: Polypeptide CDX with a high binding activity to
      an acetylcholine receptor.

<400> SEQUENCE: 4
```

```
Phe Lys Glu Ser Trp Arg Glu Ala Arg Gly Thr Arg Ile Glu Arg Gly
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Polypeptide CDX with a high binding activity to
      an acetylcholine receptor.
<220> FEATURE:
<221> NAME/KEY: misc_feature
<222> LOCATION: (2)..(6)
<223> OTHER INFORMATION: Amino acid is D-amino acid
<220> FEATURE:
<221> NAME/KEY: misc_feature
<222> LOCATION: (8)..(16)
<223> OTHER INFORMATION: Amino acid is D-amino acid

<400> SEQUENCE: 5

Gly Arg Glu Ile Arg Thr Gly Arg Ala Glu Arg Trp Ser Glu Lys Phe
1               5                   10                  15
```

METHOD FOR PREPARING BIOFILM-COATED DRUG NANOCRYSTAL AND APPLICATION THEREOF

REFERENCE TO A "SEQUENCE LISTING"

An ASCII text file of Sequence Listing is submitted separately, naming "GBBJCH025-PKG_Sequence Listing_20200903.txt", created on 09/03/2020, and sized 2,248 bytes, and the ASCII text file is incorporated herein by reference.

CROSS REFERENCE TO THE RELATED APPLICATIONS

This application is the national phase entry of International Application No. PCT/CN2018/081364, filed on Mar. 30, 2018, which is based upon and claims priority to Chinese Patent Application No. 201710207275.6, filed on Mar. 31, 2017, the entire contents of which are incorporated herein by reference.

TECHNICAL FIELD

The present disclosure belongs to the field of pharmacy, and relates to a method for preparing a biofilm-coated drug nanocrystal, and an application of the method in a construction of a nano drug delivery system of the biofilm-coated nanocrystal. Specifically, the present disclosure relates to a method for preparing a nano drug delivery system of a biofilm-coated drug nanocrystal by coating a nanocrystal of a drug directly as a rigid supporting skeleton with a biofilm, and an application of the method in preparing a nano drug delivery system of a biofilm-coated nanocrystal.

BACKGROUND

A biofilm-coated nano drug delivery system is a drug delivery system formed by coating a rigid supporting nanoparticle with a layer of biofilm, where the supporting nanoparticle is usually made of an organic polymer material or an inorganic material.

Compared with conventional delivery systems such as liposomes, polymer micelles, nanoparticles, etc., the biofilm-coated nano delivery system possesses the following advantages: 1) good biocompatibility and high safety; 2) a long action time of the systemic circulation; 3) no PEGylation modification and low immunogenicity compared with traditional long-circulation nano preparations. In addition, the biofilm-coated nano drug delivery system may also possess targeted properties by homology-directed tropisms or surface modifications using targeting molecules.

The biofilm-coated nano drug delivery system can carry drugs by adsorbing the drugs onto the biofilm or loading the drugs in the supporting skeleton. The drug-carrying method of adsorbing on the biofilm is generally suitable for substances which have specific adsorption to the biofilm. For example, owing to the natural adsorption of bacterial toxin onto erythrocyte membrane, an erythrocyte membrane-coated nanoparticle adsorbing the bacterial toxin can be used for immunoprophylaxis and treatment. However, this drug-carrying method is not suitable for most drugs. The drug-carrying method of loading the drugs in the supporting skeleton is performed by first encapsulating the drugs in nanoparticles formed by an organic polymer carrier (poly (lactic-co-glycolic acid) (PLGA) is commonly used) or an inorganic carrier (e.g. mesoporous materials), and then coating the nanoparticles with a biofilm by an extrusion method or an ultrasonic method to form a drug-carried biofilm-coated nano drug delivery system. However, carrying the drugs with the aid of the PLGA nanoparticles leads to a low drug loading capacity generally due to a poor compatibility of the drug molecules with the carrier. Although carrying the drugs using the inorganic mesoporous materials results in a relatively high drug loading capacity, the inorganic mesoporous material is limited in practical use due to a non-degradability and a poor biocompatibility of the inorganic carrier.

Drug nanocrystals are nanoscale rigid drug crystals formed in a crystallization of drug molecules. As a pharmaceutical intermediate for improving drug dissolution and drug bioavailability, the drug nanocrystals have been widely used in the research and development of oral preparations. In addition, the drugs exist in the form of nanocrystals, showing a sustained release capability.

The present disclosure provides a method for preparing a biofilm-coated nano drug delivery system by using a rigid drug nanocrystal as a supporting skeleton. In the method, the drug nanocrystal replaces the conventional PLGA or inorganic mesoporous materials used in the prior preparation of biofilm-coated nano drug delivery systems, which not only provides a supporting structure required for the biofilm-coated nano drug delivery system, but also realizes drug carrying. The nano drug delivery system of the biofilm-coated drug nanocrystals constructed by the method has the following advantages: 1) the drug carrying capacity is high, which can meet the dosage requirements of clinical drugs; 2) the use of carrier materials is avoided, which improves the biocompatibility and safety of the drug delivery system; 3) the specific surface energy of the drug nanocrystal is reduced, and the stability of the drug nanocrystal is increased; and 4) both the sustained release property of the drug nanocrystal and the long in vivo circulation of the biofilm-coated nano drug delivery system are achieved. Therefore, the method has a great potential application value.

SUMMARY

The present disclosure provides a method for preparing a biofilm-coated drug nanocrystal.

Before describing the present invention, the terms used herein are defined as follows:

The term arginyl-glycyl-aspartic acid (RGD) refers to a polypeptide having a high binding activity to integrin.

The term tripeptide proline-valine-alanine (VAP) refers to a polypeptide having a high binding activity to a glucose-regulated protein GRP78.

The term tetrapeptide tryptophan-proline-valine-alanine (WVAP) refers to a polypeptide having a high binding activity to both a quorum sensing receptor and the glucose-regulated protein GRP78.

The term heptapeptide ATWLPPR (A7R) refers to a polypeptide as set forth in SEQ ID NOS: 1, 2, and 3 having a high binding activity to both vascular endothelial growth factor receptor-2 and neuropilin-1.

The term FKESWREARGTRIERG (CDX) refers to a polypeptide as set forth in SEQ ID NOS: 4 and 5 having a high binding activity to an acetylcholine receptor.

The term U87 cells refer to human U87 malignant glioma cells.

The term PLGA refers to poly(lactic-co-glycolic acid).

The term F127 refers to poloxamer, a polyoxyethylene polyoxypropylene ether block copolymer.

The term PEG refers to polyethylene glycol.

The term DSPE refers to distearoylphosphatidylethanolamine.

The term PBS refers to a phosphate buffered saline solution.

The term FBS refers to a fetal bovine serum.

In a first aspect of the present invention, a nano drug delivery system is provided. The nano drug delivery system includes a biofilm-coated drug nanocrystal, wherein, a drug exists in a physical form of a nanocrystal, which is directly used as a rigid supporting skeleton, and is filled in a biofilm.

According to the nano drug delivery system in the first aspect of the present invention, the drug nanocrystal is both configured as a skeleton material and a drug reservoir.

According to the nano drug delivery system in the first aspect of the present invention, the drug nanocrystal is a nanoscale crystal formed by a treatment of a drug by a physical or chemical method.

According to the nano drug delivery system in the first aspect of the present invention, the drug nanocrystal has a particle size of 10-1000 nm, preferably 10-200 nm.

According to the nano drug delivery system in the first aspect of the present invention, the drug is a therapeutic drug and % or a diagnostic agent.

Preferably, the therapeutic drug is one or more selected from the group consisting of: an anti-tumor drug, an anti-infective drug, an anti-cardiovascular disease drug, an anti-lymphatic system disorder drug, an anti-immune system disorder drug, and an analgesic drug, which can be prepared into the nanocrystal by the physical or chemical method.

Preferably, the anti-tumor drug is one selected from the group consisting of: a taxane drug such as paclitaxel, etc., an anthracycline drug such as doxorubicin, etc., a camptothecin drug, a vincristine drug, and a zomib drug such as bortezomib, etc., a platinum-based drug such as cisplatin, etc., irinotecan and/or a parthenolide drug. The anti-infective drug is one selected from the group consisting of: ceftriaxone, cefoxitin, aztreonam, streptomycin, amphotericin B, vancomycin, tigecycline, teicoplanin, moroxydine, vidarabine and acyclovir (sold under the trade name Zovirax). The anti-cardiovascular disease drug is one selected from the group consisting of: ganglioside, ferulic acid, ligustrazine, troxerutin, and sodium ozagrel. The anti-lymphatic system disorder drug is panobinostat. The anti-immune system disorder drug is one selected from the group consisting of: methylprednisolone and cyclosporine. The analgesic drug is one selected from the group consisting of morphine and methadone.

Most preferably, the drug is irinotecan, docetaxel or cabazitaxel.

Preferably, the diagnostic agent is one or more selected from the group consisting of: a fluorescent substance, a near-infrared dye, and a magnetic resonance imaging agent, which can be prepared into the nanocrystal by the physical or chemical method.

According to the nano drug delivery system in the first aspect of the present invention, the biofilm has a membrane structure with a lipid bilayer.

Preferably, the biofilm is a natural cell membrane or an artificial biofilm.

More preferably, the natural cell membrane is one or more selected from the group consisting of: an erythrocyte membrane, a platelet membrane, a macrophage membrane, a leukocyte membrane, and a tumor cell membrane. The artificial biofilm is a liposome membrane.

Further preferably, the biofilm is one or more selected from the group consisting of: an erythrocyte membrane, a platelet membrane, and a tumor cell membrane.

According to the nano drug delivery system in the first aspect of the present invention, a surface of the nano drug delivery system is further modified by a targeting molecule to construct the nano drug delivery system as a nano drug delivery system of the biofilm-coated nanocrystal with an active targeting capability.

Preferably, the targeting molecule is a polypeptide targeting molecule.

More preferably, the polypeptide targeting molecule is one or more selected the group consisting of: RGD, VAP, WVAP, A7R, and CDX.

In a second aspect of the present invention, a method for preparing the nano drug delivery system described in the first aspect of the present invention is provided. The method includes: directly using the drug nanocrystal in the physical form as the rigid supporting skeleton, and filling in the biofilm.

In a third aspect of the present invention, an application of the nano drug delivery system in the first aspect of the present invention in preparing a medicament for a in-vivo therapeutic and/or a diagnostic product is provided.

In a fourth aspect of the present invention, a method of using a medicament for treating and/or diagnosing a disease in vivo is provided, including administering the nano drug delivery system in the first aspect of the present invention to a subject in demand.

According to the application in the third aspect of the present invention or the method in the fourth aspect of the present invention, using the medicament for a treatment and/or a diagnosis in vivo is using the medicament for a targeted treatment and/or a targeted diagnosis in vivo.

The present invention provides an application of the method of the present invention in a preparation of the nano drug delivery system of the biofilm-coated nanocrystal.

Specifically, the method for preparing the biofilm-coated drug nanocrystal provided by the present invention includes: constructing the drug into the nanocrystal, and then directly using the nanocrystal as the rigid supporting skeleton to coat with the biofilm to obtain the nano drug delivery system of the biofilm-coated nanocrystal.

The nanocrystal of the drug may be obtained by a physical or chemical treatment, and a particle size of the obtained nanocrystal is controlled to be of 10-1000 nm, preferably 10-200 nm. The drug nanocrystal is composed of a therapeutic drug or a diagnostic agent. The therapeutic drug is one selected from the group consisting of an anti-tumor drug (e.g., a taxane drug such as paclitaxel and the like, an anthracycline drug such as doxorubicin and the like, a camptothecin drug, a vincristine drug, and a zomib drug such as bortezomib and the like, a platinum-based drug such as cisplatin and the like, irinotecan, a parthenolide drug, etc.), an anti-infective drug (e.g., ceftriaxone, cefoxitin, aztreonam, streptomycin, amphotericin B, vancomycin, tigecycline, teicoplanin, moroxydine, vidarabine, acyclovir (sold under the trade name Zovirax), etc.), an anti-cardiovascular disease drug (e.g., ganglioside, ferulic acid, ligustrazine, troxerutin, sodium ozagrel, etc.), an anti-lymphatic system disorder drug (e.g., panobinostat, etc.), an anti-immune system disorder drug (e.g., methylprednisolone, cyclosporine, etc.), and an analgesic drug (e.g., morphine, methadone, etc.), which can be prepared into the nanocrystal by physical or chemical methods. The diagnostic agent is one selected from the group consisting of: a fluorescent substance (e.g., fluorescein, rhodamine, etc.), a near-infrared dye (e.g., cy5.5, IR820, DiR, etc.), and a magnetic resonance imaging agent (e.g., a Gd agent, ferric oxide, etc.), which can be prepared into the nanocrystal by physical or chemical methods. The biofilm has a membrane structure with a lipid bilayer, which may be a natural cell membrane, such as an erythrocyte membrane, a platelet membrane, a macrophage membrane, a leukocyte membrane, a tumor cell membrane and the like; or an artificial biofilm such as a liposome membrane and the like.

A nano drug delivery system of an erythrocyte membrane-coated irinotecan nanocrystal, a nano drug delivery system of a platelet membrane-coated irinotecan nanocrystal, a nano drug delivery system of an erythrocyte membrane-coated docetaxel nanocrystal, and a nano drug delivery system of an RGD modified erythrocyte membrane-coated docetaxel nanocrystal are constructed by the method provided by the present invention.

The nano drug delivery system of the erythrocyte membrane-coated docetaxel nanocrystal and the nano drug delivery system of the RGD modified erythrocyte membrane-coated docetaxel nanocrystal of the present invention can be used for a tumor-targeted drug delivery in vivo for an anti-tumor treatment.

The present invention provides a method for preparing a biofilm-coated drug nanocrystal, an application of the method in a construction of a nano drug delivery system of the biofilm-coated nanocrystal, and a nano drug delivery system of an erythrocyte membrane-coated docetaxel nanocrystal and a nano drug delivery system of an RGD modified erythrocyte membrane-coated docetaxel nanocrystal constructed by the method as a basis for a tumor treatment. Test results of the present invention indicate that: the nano drug delivery system of the biofilm-coated drug nanocrystal prepared by the method of the present invention has a distinct nuclear-membrane structure shown by transmission electron microscope (TEM), moreover, the stability of the drug nanocrystal is significantly improved, indicating that the drug nanocrystals are successfully coated by the biofilm; the in vitro release result shows that the nano drug delivery system of the biofilm-coated drug nanocrystal has a remarkable drug sustained release property; the in vivo pharmacokinetics result indicates that the nano drug delivery system of the biofilm-coated drug nanocrystal has the advantage of long circulation, which significantly prolongs the circulation time of the drug in the body. The nano drug delivery system of the biofilm-coated/targeting molecular modified biofilm-coated drug nanocrystal can be enriched in tumor tissue by a passive or active targeting, and has a stronger inhibitory effect on tumor growth. In addition, the nano drug delivery system of the biofilm-coated drug nanocrystal is safer than commercially available formulations and drug nanocrystals. The above results indicate that the method for preparing the biofilm-coated drug nanocrystal provided by the present invention can be used for preparing the nano drug delivery system of the biofilm-coated drug nanocrystal, and possesses greater advantages compared to the currently existing method for constructing biofilm-coated nano drug delivery system and the drug-carrying thereof, and therefore has good application prospects.

1. Preparation and Characterization of Nano Drug Delivery Systems of Erythrocyte Membrane-Coated/Platelet Membrane-Coated/Tumor Cell Membrane-Coated Irinotecan/Cabazitaxel Nanocrystal Target cells (erythrocyte or platelet) or tumor cells of a living animal are taken to collect cell membranes to prepare a cell membrane suspension. An appropriate amount of a surfactant is added to irinotecan/cabazitaxel to form a drug nanocrystal suspension after film-forming and hydration. The cell membrane suspension is mixed with the drug nanocrystal suspension for an ultrasonic treatment to obtain the nano drug delivery system of the biofilm-coated irinotecan/cabazitaxel nanocrystal. The morphology is characterized by TEM.

2. Preparation and Characterization of Nano Drug Delivery Systems of Erythrocyte Membrane-Coated/RGD, VAP, WVAP, A7R, or CDX Modified Erythrocyte Membrane-Coated Docetaxel Nanocrystal The nano drug delivery system of the erythrocyte membrane-coated docetaxel nanocrystal is prepared and characterized by the same method described above.

Modification of RGD, VAP, WVAP, A7R or CDX is performed by first modifying the surface of the nano drug delivery system of the erythrocyte membrane-coated docetaxel nanocrystal with streptavidin by a lipid insertion method, and then incubating with biotinylated RGD, biotinylated VAP, biotinylated WVAP, biotinylated A7R or biotinylated CDX to obtain the RGD, VAP, WVAP, A7R, or CDX modified erythrocyte membrane-coated docetaxel nanocrystal. The in vitro release of the drug is determined by a dialysis bag method.

3. In Vivo Pharmacokinetic Determination of Nano Drug Delivery System of Erythrocyte Membrane-Coated Docetaxel Nanocrystal and Nano Drug Delivery System of RGD Modified Erythrocyte Membrane-Coated Docetaxel Nanocrystal Institute of Cancer Research (ICR) mice are administrated with a commercially available docetaxel injection, a docetaxel nanocrystal, the nano drug delivery system of the erythrocyte membrane-coated docetaxel nanocrystal, and the nano drug delivery system of the RGD modified erythrocyte membrane-coated docetaxel nanocrystal by tail vein injections. Bloods are collected after a certain time, concentrations of the drugs in the bloods are determined by a high-performance liquid chromatography (HPLC) method, and pharmacokinetic curves are plotted.

4. In Vivo Tissue Distribution Determination of Nano Drug Delivery System of Erythrocyte Membrane-Coated Docetaxel Nanocrystal and Nano Drug Delivery System of RGD Modified Erythrocyte Membrane-Coated Docetaxel Nanocrystal U87 subcutaneous xenograft model nude mice or U87 intracerebral orthotopic tumor model nude mice are administered with a commercially available docetaxel injection, the nano drug delivery system of the erythrocyte membrane-coated docetaxel nanocrystal, and the nano drug delivery system of the RGD modified erythrocyte membrane-coated docetaxel nanocrystal by tail vein injections. The tissues, organs and whole bloods are collected after a certain time, and the concentrations of the drugs in the tissues and the bloods are determined by HPLC.

5. In Vitro Pharmacodynamic Evaluation of Nano Drug Delivery System of Erythrocyte Membrane-Coated Docetaxel Nanocrystal and Nano Drug Delivery System of RGD Modified Erythrocyte Membrane-Coated Docetaxel Nanocrystal In vitro growth inhibition effects of a commercially available docetaxel injection, a docetaxel nanocrystal, the nano drug delivery system of the erythrocyte membrane-coated docetaxel nanocrystal, and the nano drug delivery system of the RGD modified erythrocyte membrane-coated docetaxel nanocrystal on glioma cell U87 are investigated by 3-(4, 5-dimethyl-2-thiazolyl)-2, 5-diphenyltetrazolium bromide (MTT) assay.

6. In Vivo Pharmacodynamic Evaluation of Nano Drug Delivery System of Erythrocyte Membrane-Coated Docetaxel Nanocrystal and Nano Drug Delivery System of RGD Modified Erythrocyte Membrane-Coated Docetaxel Nanocrystal U87 subcutaneous xenograft model nude mice are administered with normal saline, a commercially available docetaxel injection, a docetaxel nanocrystal, the nano drug delivery system of the erythrocyte membrane-coated docetaxel nanocrystal, and the nano drug delivery system of the RGD modified erythrocyte membrane-coated docetaxel nanocrystal by tail vein injections. The anti-tumor effect in vivo is evaluated by using tumor volume and survival time as indicators.

U87 intracerebral orthotopic tumor model nude mice are administered with normal saline, a commercially available docetaxel injection, the nano drug delivery system of the erythrocyte membrane-coated docetaxel nanocrystal, and the nano drug delivery system of the RGD modified erythrocyte membrane-coated docetaxel nanocrystal by tail vein injections. The anti-tumor effect in vivo is evaluated by using survival time as an indicator.

7. Safety Evaluation of Nano Drug Delivery System of Erythrocyte Membrane-Coated Docetaxel Nanocrystal and Nano Drug Delivery System of RGD Modified Erythrocyte Membrane-Coated Docetaxel Nanocrystal Normal nude mice are administered with normal saline, a commercially available docetaxel injection, the nano drug delivery system of the erythrocyte membrane-coated docetaxel nanocrystal, and the nano drug delivery system of the RGD modified erythrocyte membrane-coated docetaxel nanocrystal by tail vein injections. In vivo safety is evaluated by using the leukocyte level of whole blood and the creatinine clearance rate of mice as indicators.

BRIEF DESCRIPTION OF THE DRAWINGS

as can be seen from the figure, a irinotecan nanocrystal in FIG. 1A is rod-shaped; the nano drug delivery system of the erythrocyte membrane-coated irinotecan nanocrystal in FIG. 1B and the nano drug delivery system of the platelet membrane-coated irinotecan nanocrystal in FIG. 1C are spherical with a particle size of about 40 nm.

as can be seen from the figure, a docetaxel nanocrystal in FIG. 2A is spherical with a particle size of about 30 nm; the nano drug delivery system of the erythrocyte membrane-coated docetaxel nanocrystal in FIG. 2B is spherical with a distinct nuclear-membrane structure and a particle size of about 70 nm.

the figure shows releases of a docetaxel nanocrystal (DTX NCs), the nano drug delivery system of the erythrocyte membrane-coated docetaxel nanocrystal (RBC/DTX NCs), and the nano drug delivery system of the RGD modified erythrocyte membrane-coated docetaxel nanocrystal (RGD-RBC/DTX NCs) in PBS solution with a pH of 7.4. The results show that docetaxel have a good sustained release capability after being coated with erythrocyte membrane, and the modification of the targeting molecule has no effect on the release.

as can be seen from the figure and table, whether being modified with RGD or not, the nano drug delivery system of the erythrocyte membrane-coated docetaxel nanocrystal (RBC/DTX NCs) has a longer circulation time in mice, and the modification of the targeting molecule has no significant effect on the pharmacokinetic behavior in the mice, compared with a docetaxel nanocrystal (DTX NCs) and a commercially available docetaxel injection (DTX).

as can be seen from the figure, whether being modified with RGD or not, the nano drug delivery system of the erythrocyte membrane-coated docetaxel nanocrystal (RBC/DTX NCs) has a reduced distribution in livers of mice, and an increased distribution in bloods and tumors, and targeting molecular modification can significantly increase an accumulation of drugs at a tumor site, compared with a commercially available docetaxel injection (DTX).

as can be seen from the figure, whether being modified with RGD or not, the nano drug delivery system of the erythrocyte membrane-coated docetaxel nanocrystal (RBC/DTX NCs) has a reduced distribution in livers of mice, and an increased distribution in bloods, and targeting molecular modification can carry the nano drug delivery system across a blood-brain tumor barrier and significantly increase an accumulation of drugs at a tumor site, compared with a commercially available docetaxel injection (DTX).

as can be seen from the figure, U87 cells are incubated with a commercially available docetaxel injection (DTX), a docetaxel nanocrystal (DTX NCs), the nano drug delivery system of the erythrocyte membrane-coated docetaxel nanocrystal (RBC-DTX NCs), and the nano drug delivery system of the RGD modified erythrocyte membrane-coated docetaxel nanocrystal (RGD-RBC/DTX NCs) for 48 h, respectively, and their $IC_{50}$ are 41.6 nM, 49.7 nM, 233.8 nM, and 13.8 nM, respectively. The results show that, whether being modified with RGD or not, RBC/DTX NCs can inhibit the growth of the U87 cells in vitro.

An in vitro anti-tumor activity of the RGD modified RBC/DTX NCs is much better than that of the group without target.

FIGS. 8A-8D show anti-U87 subcutaneous tumor evaluations of a nano drug delivery system of an erythrocyte membrane-coated docetaxel nanocrystal and a nano drug delivery system of an RGD modified erythrocyte membrane-coated docetaxel nanocrystal:

FIGS. 10A-10B show in vivo safety evaluations of a nano drug delivery system of an erythrocyte membrane-coated docetaxel nanocrystal and a nano drug delivery system of an RGD modified erythrocyte membrane-coated docetaxel nanocrystal:

DETAILED DESCRIPTION OF THE EMBODIMENTS

The following embodiments are provided to help a further understanding of the present invention, but the present invention is not limited to the scope of the following description.

Embodiment 1

Figure 1A:
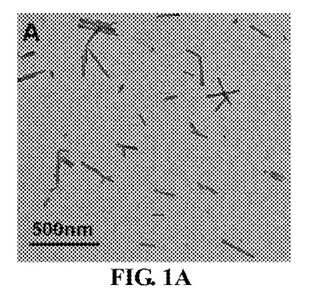
FIGS. 1A-IC show electron micrographs of a nano drug delivery system of an erythrocyte membrane-coated irinotecan nanocrystal and a nano drug delivery system of a platelet membrane-coated irinotecan nanocrystal.
Figure 1B:
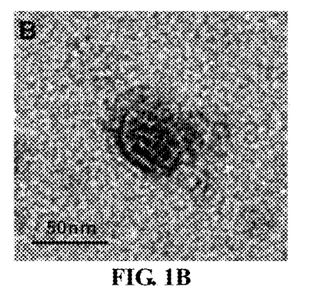
Figure 1C:
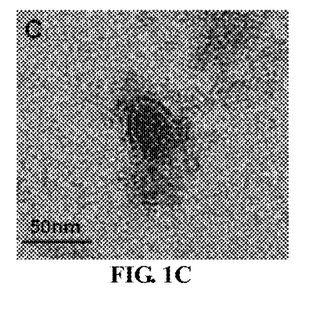

Preparation and Characterization of Nano Drug Delivery System of Erythrocyte Membrane-Coated/Platelet Membrane-Coated/Tumor Cell Membrane-Coated Irinotecan/Cabazitaxel Nanocrystal 1. Preparation and Characterization of Nano Drug Delivery System of Erythrocyte Membrane-Coated Irinotecan Nanocrystal Whole blood of a male ICR mouse was taken, centrifuged at 1000 g/min for 5 min at 4° C. The serum and leukocytes at an upper layer were discarded. The erythrocytes at a lower layer were washed with 1×PBS, and then resuspended in 0.25×PBS at 4° C. for 30 min. The hemoglobin was removed by centrifugation at 15000 g/min for 7 min at 4° C. The obtained light red erythrocyte membrane was resuspended and stored in double distilled water, and the membrane protein concentration thereof was detected by a bicinchoninic acid (BCA) kit. 4 mg of irinotecan and an appropriate amount of surfactant F127 were weighed and placed in a 25 mL eggplant-shaped flask, followed by adding an appropriate amount of methanol to dissolve for film forming and hydration to obtain an irinotecan nanocrystal with a good dispersibility. The erythrocyte membrane suspension was ultrasonicated at 100 W for 3 min to obtain erythrocyte membrane vesicles. Then, 4 mg/mL of an irinotecan nanocrystal solution was mixed with the erythrocyte membrane vesicles (2:1, w/w) and then ultrasonicated to obtain the nano drug delivery system of the erythrocyte membrane-coated irinotecan nanocrystal. The morphology was observed by a uranyl acetate negative stain electron microscopy method. The results are shown in FIGS. 1A-1C.

2. Preparation and Characterization of Nano Drug Delivery System of Platelet Membrane-Coated Irinotecan Nanocrystal Whole blood of a male ICR mouse was taken, centrifuged at 300 g/min for 5 min at 4° C. to obtain a first supernatant, followed by centrifuging at 2000 g/min for 5 min, and a second supernatant was discarded. The platelets at a lower layer were washed with double distilled water, and then repeatedly frozen and thawed three times, followed by centrifuging at 20000 g/min for 7 min. The obtained white platelet membrane was resuspended and stored in double distilled water, and the membrane protein concentration thereof was detected by a BCA kit. The platelet membrane suspension was treated with an irinotecan nanocrystal solution as above to obtain the nano drug delivery system of the platelet membrane-coated irinotecan nanocrystal. The morphology was observed by a uranyl acetate negative stain electron microscopy method. The results are shown in FIGS. 1A-1C.

3. Preparation of Nano Drug Delivery System of Tumor Cell Membrane-Coated Irinotecan Nanocrystal Tumor cells (U87) were transferred to a buffer solution (obtained by dissolving 20.5 g of mannitol and 13 g of sucrose in 500 mL of Tris(hydroxymethyl)aminomethane hydrochloride (Tris-HCl) buffer, pH 7.5), and centrifuged at 800 g/min for 5 min. A first supernatant was discarded, and the residue was added with the above buffer, followed by adding ethylenediaminetetraacetic acid and a protease inhibitor. Ultrasonic homogenization was performed, and the homogenized solution was centrifuged for 5 min at 800 g/min to obtain a second supernatant, followed by centrifuging at 8000 g/min at −20° C. for 25 min to obtain a third supernatant. Then, the third supernatant was centrifuged at 30000 g/min at −20° C. for 35 min to obtain tumor cell membranes by discarding a fourth supernatant. The tumor cell membranes were resuspended and stored in a 0.2 mM ethylenediaminetetraacetic acid solution, and the membrane protein concentration thereof was detected by a BCA kit. The tumor cell membrane suspension was treated with an irinotecan nanocrystal solution as above to obtain the nano drug delivery of the tumor cell membrane-coated irinotecan nanocrystal.

4. Preparation of Nano Drug Delivery System of Erythrocyte Membrane-Coated/Platelet Membrane-Coated/Tumor Cell Membrane-Coated Cabazitaxel Nanocrystal The preparation method was the same as the nano drug delivery system of the erythrocyte membrane-coated/platelet membrane-coated/tumor cell membrane-coated irinotecan nanocrystal.

Embodiment 2

Figure 2A:
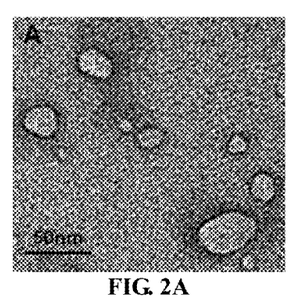
FIGS. 2A-2B show electron micrographs of a nano drug delivery system of an erythrocyte membrane-coated docetaxel nanocrystal.
Figure 2B:
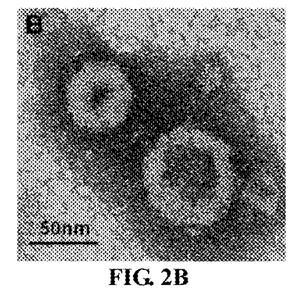

Preparation and Characterization of Nano Drug Delivery System of Erythrocyte Membrane-Coated/RGD, VAP, WVAP, A7R, or CDX Modified Erythrocyte Membrane-Coated Docetaxel Nanocrystal 1. Preparation and Characterization of Nano Drug Delivery System of Erythrocyte Membrane-Coated Docetaxel Nanocrystal The methods of the preparation and characterization were the same as the nano drug delivery system of the erythrocyte membrane-coated irinotecan nanocrystal. The results are shown in FIGS. 2A-2B.

2. Preparation of Nano Drug Delivery System of RGD Modified Erythrocyte Membrane-Coated Docetaxel Nanocrystal The preparation process was basically the same as the nano drug delivery system of the erythrocyte membrane-coated docetaxel nanocrystal. The RGD modification method was as follows. 40 μL of streptavidin-PEG$_{3400}$-DSPE PBS solution (5 mg/mL) was incubated with erythrocyte membrane vesicles obtained from 100 μL of whole blood in a water bath at 37° C. for 30 min to obtain streptavidin-erythrocyte membrane vesicles. The obtained streptavidin-erythrocyte membrane vesicles were mixed with docetaxel nanocrystals and then ultrasonicated to obtain a nano drug delivery system of a streptavidin-modified erythrocyte membrane-coated nanocrystal. Then, 100 μL of biotin-PEG$_{3500}$-RGD PBS solution (0.1 mg/mL) was added and incubated in the water bath at 37° C. for 10 min to obtain the nano drug delivery system of the RGD-modified erythrocyte membrane-coated docetaxel nanocrystal.

3. Preparation of Nano Drug Delivery System of VAP, WVAP, A7R, or CDX Modified Erythrocyte Membrane-Coated Docetaxel Nanocrystal The preparation method was the same as the nano drug delivery system of the RGD-modified erythrocyte membrane-coated docetaxel nanocrystal.

Embodiment 3

Figure 3:
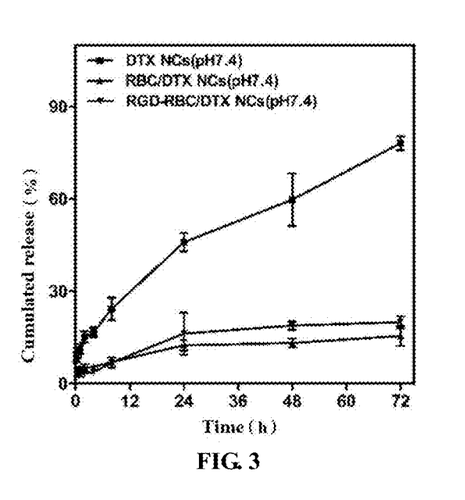
FIG. 3 shows in vitro release curves of a nano drug delivery system of an erythrocyte membrane-coated docetaxel nanocrystal and a nano drug delivery system of an RGD modified erythrocyte membrane-coated docetaxel nanocrystal.

In Vitro Release Tests of Nano Drug Delivery System of Erythrocyte Membrane-Coated Docetaxel Nanocrystal and Nano Drug Delivery System of RGD Modified Erythrocyte Membrane-Coated Docetaxel Nanocrystal The in vitro release was determined by a dialysis bag method. 0.3 mL of a docetaxel nanocrystal (DTX NCs), the nano drug delivery system of the erythrocyte membrane-coated docetaxel nanocrystal (RBC/DTX NCs), and the nano drug delivery system of the RGD modified erythrocyte membrane-coated docetaxel nanocrystal (RGD-RBC/DTX NCs) were respectively placed in a dialysis bag (molecular weight cut-off of 7 kDa) and sealed, and then placed in 6 mL of PBS solution having a pH of 7.4 (containing 1% sodium dodecyl sulfate) and shaken at 37° C. 0.2 mL of release medium was respectively taken at 15 min, 30 min, 1 h, 1.5 h, 2 h, 4 h, 8 h, 24 h, 48 h and 72 h, and a same volume of fresh medium was added. The taken solution was properly diluted, the docetaxel concentration was determined by an HPLC method, and the release curve was plotted. The results are shown in FIG. 3.

Embodiment 4

Figure 4:
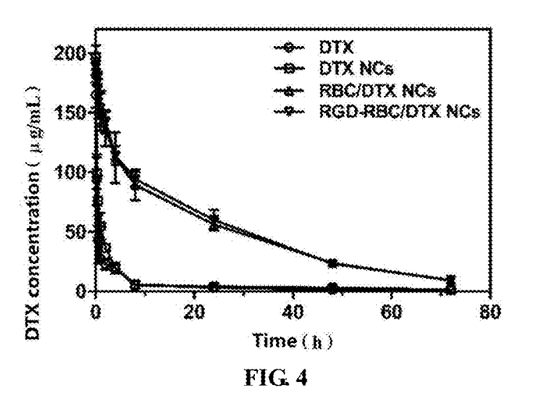
FIG. 4 shows in vivo pharmacokinetic curves of a nano drug delivery system of an erythrocyte membrane-coated docetaxel nanocrystal and a nano drug delivery system of an RGD modified erythrocyte membrane-coated docetaxel nanocrystal.

In Vivo Pharmacokinetic Tests of Nano Drug Delivery System of Erythrocyte Membrane-Coated Docetaxel Nanocrystal and Nano Drug Delivery System of RGD Modified Erythrocyte Membrane-Coated Docetaxel Nanocrystal ICR mice were administered with 150 μL of a commercially available docetaxel injection (DTX), a docetaxel nanocrystal (DTX NCs), the nano drug delivery system of the erythrocyte membrane-coated docetaxel nanocrystal (RBC/DTX NCs), and the nano drug delivery system of the RGD modified erythrocyte membrane-coated docetaxel nanocrystal (RGD-RBC,DTX NCs) by tail vein injections, respectively. 50 μL of whole blood was respectively taken at 5 min, 15 min, 30 min, 1 h, 2 h, 4 h, 8 h, 24 h, 48 h and 72 h, extracted twice with a solution composed of diethyl ether and tetrahydrofuran at a volume ratio of 1:4, evaporated and dried, and redissolved with acetonitrile for HPLC analysis. The results are shown in FIG. 4 and Table.

TABLE

Parameters of nano drug delivery system of erythrocyte membrane-coated docetaxel nanocrystal and nano drug delivery system of RGD modified erythrocyte membrane-coated docetaxel nanocrystal

| Pharmacokinetic parameter | DTX | DTX NCs | RBC/DTX NCs | RGD-RBC/DTX NCs |
|---|---|---|---|---|
| $T_{1/2}\ \beta$ (h) | 3.7 ± 1.5 | 2.5 ± 0.6 | 20.4 ± 2.2 | 19.7 ± 1.1 |
| $AUC_{0-\infty}$ (mg/L × h) | 163.2 ± 48.1 | 143.1 ± 47.7 | 3714.5 ± 132.2 | 3852.3 ± 139.3 |

Embodiment 5

Figure 5:
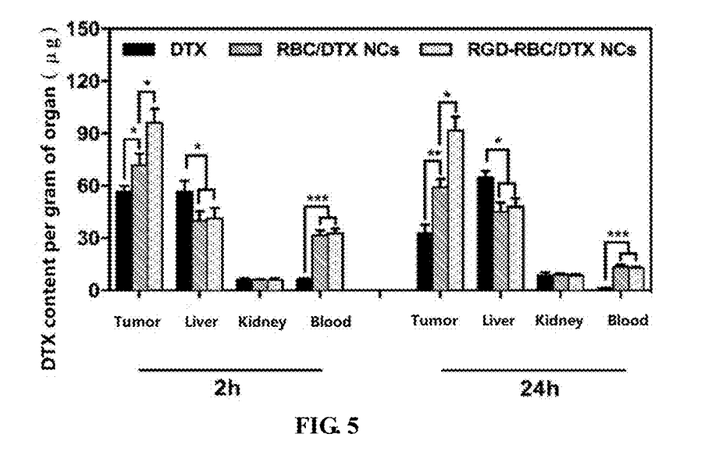
FIG. 5 is a bar graph showing tissue distributions of a nano drug delivery system of an erythrocyte membrane-coated docetaxel nanocrystal and a nano drug delivery system of an RGD modified erythrocyte membrane-coated docetaxel nanocrystal in U87 subcutaneous xenograft model mice.
Figure 6:
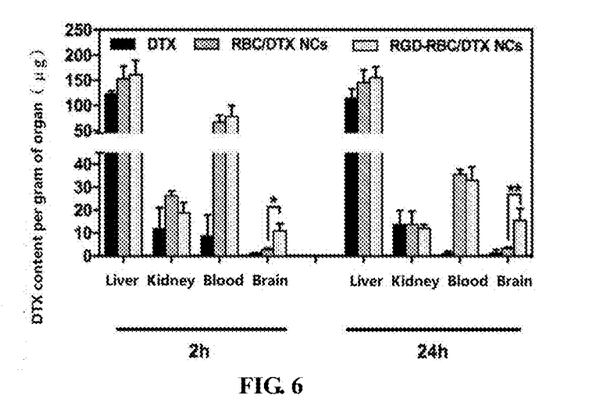
FIG. 6 is a bar graph showing tissue distributions of a nano drug delivery system of an erythrocyte membrane-coated docetaxel nanocrystal and a nano drug delivery system of an RGD modified erythrocyte membrane-coated docetaxel nanocrystal in U87 intracerebral orthotopic tumor model nude mice.

In Vivo Tissue Distribution Tests of Nano Drug Delivery System of Erythrocyte Membrane-Coated Docetaxel Nanocrystal and Nano Drug Delivery System of RGD Modified Erythrocyte Membrane-Coated Docetaxel Nanocrystal U87 subcutaneous xenograft/orthotopic tumor animal models were constructed, and were administered with 150 μL of a commercially available docetaxel injection (DTX), the nano drug delivery system of the erythrocyte membrane-coated docetaxel nanocrystal (RBC/DTX NCs), and the nano drug delivery system of the RGD modified erythrocyte membrane-coated docetaxel nanocrystal (RGD-RBC/DTX NCs) by tail vein injections, respectively. Tissue and whole blood were taken at 2 h and 24 h, respectively. The tissue was homogenized, extracted twice with a solution composed of diethyl ether and tetrahydrofuran at a volume ratio of 1:4, evaporated and dried, and redissolved with acetonitrile for HPLC analysis. The results are shown in FIGS. 5 and 6.

Embodiment 6

Figure 7:
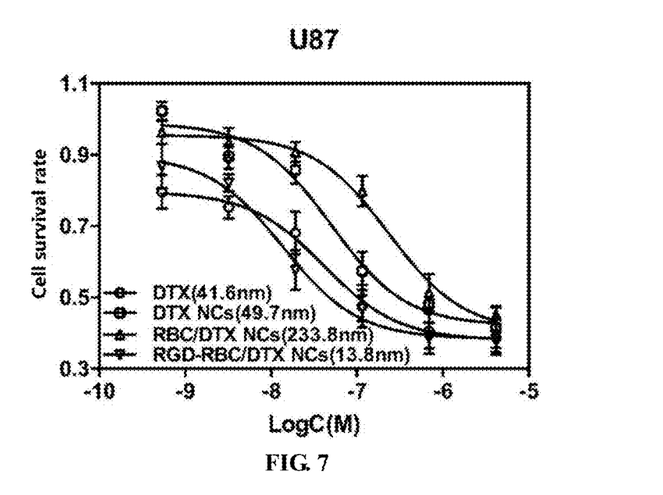
FIG. 7 shows in vitro anti-U87 cell activity curves of a nano drug delivery system of an erythrocyte membrane-coated docetaxel nanocrystal and a nano drug delivery system of an RGD modified erythrocyte membrane-coated docetaxel nanocrystal.

In Vitro Pharmacodynamic Tests of Nano Drug Delivery System of Erythrocyte Membrane-Coated Docetaxel Nanocrystal and Nano Drug Delivery System of RGD Modified Erythrocyte Membrane-Coated Docetaxel Nanocrystal In vitro growth inhibition effects of a commercially available docetaxel injection (DTX), a docetaxel nanocrystal (DTX NCs), the nano drug delivery system of the erythrocyte membrane-coated docetaxel nanocrystal (RBC,DTX NCs), and the nano drug delivery system of the RGD modified erythrocyte membrane-coated docetaxel nanocrystal (RGD-RBC/DTX NCs) on U87 tumor cells are determined by MTT assay. The U87 cells in logarithmic growth phase were digested with 0.25% trypsin and blown into single cells. The cells were suspended in Dulbecco's modified Eagle's medium (DMEM) containing 10% FBS, and inoculated in a 96-well cell culture plate at a density of 3000 cells/well and a volume of 0.2 mL/well. Three wells were remained to add with the medium without the cells as blank wells. A culture was performed in a carbon dioxide incubator for 24 h. Each group of the drugs was serially diluted six times with the cell culture medium. The cell culture medium in the 96-well cell culture plate was removed, and 200 μL of each of the the serial concentrations of the drug solutions was added to each well. Three repeated wells were set for each concentration, and three wells were remained to merely add with the culture medium as control wells. After culturing for 48 h, 20 μL of MTT reagent (5 mg/mL) was added to the test wells, control wells and blank wells for incubation for 4 h, and then the culture medium was discarded. 150 μL of dimethyl sulfoxide was added to each well, and shaken to sufficiently dissolving the generated blue-violet crystals. The absorbance (A) of each well was measured by a microplate reader at 490 nm. The cell survival rate was calculated according to the following formula:

Survival rate=$(A_{490\ test\ well} - A_{490\ blank\ well})/(A_{490\ control\ well} - A_{490\ blank\ well}) \times 100\%$ The survival rate over the logarithm of drug concentration were plotted by GraphPad Prism software (FIG. 7), and the half maximal inhibitory concentration ($IC_{50}$) was calculated.

Embodiment 7

Figure 8A:
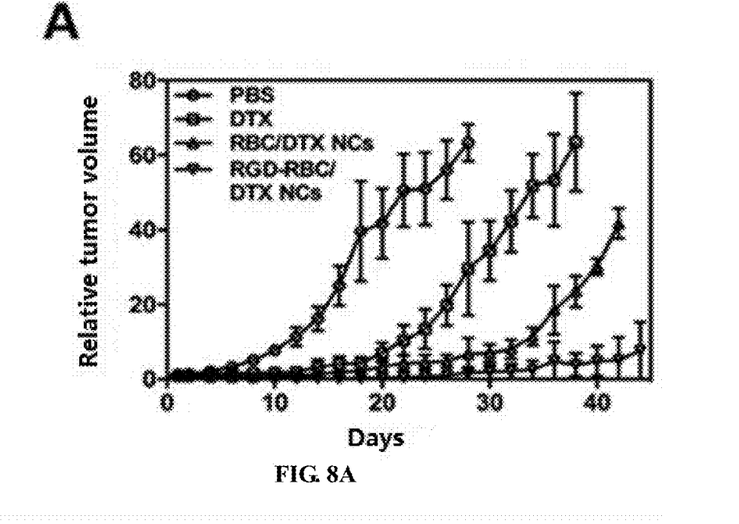
FIG. 8A shows changing curves of tumor volumes of U87 subcutaneous transplanted nude mice over time.
Figure 8B:
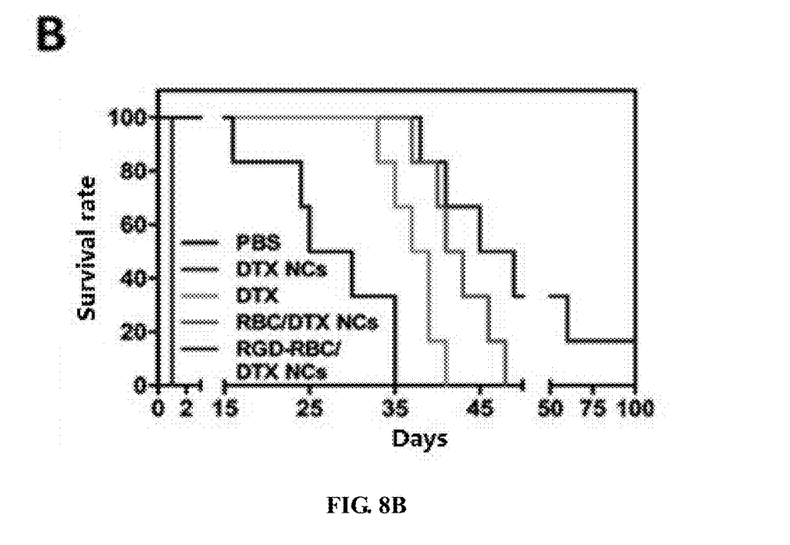
FIG. 8B shows survival curves of U87 subcutaneous transplanted nude mice over time.
Figure 8C:
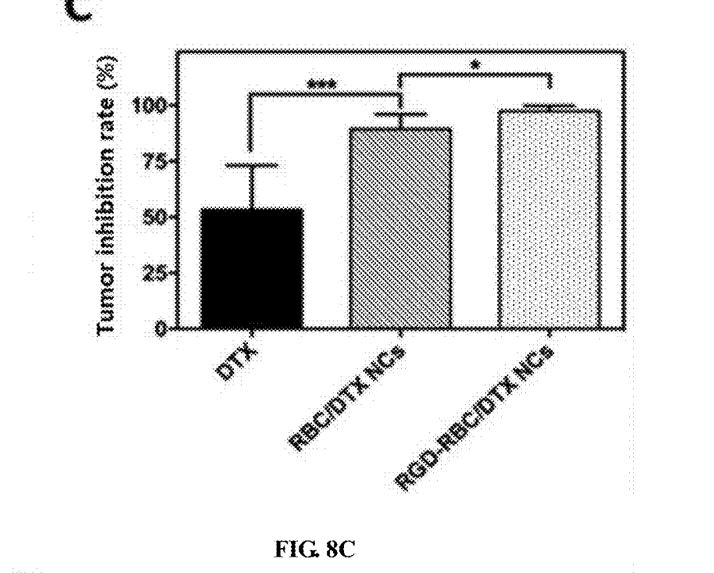
FIG. 8C is a comparison of tumor inhibition rates of various groups on 28$^{th}$ day after administration.
Figure 8D:
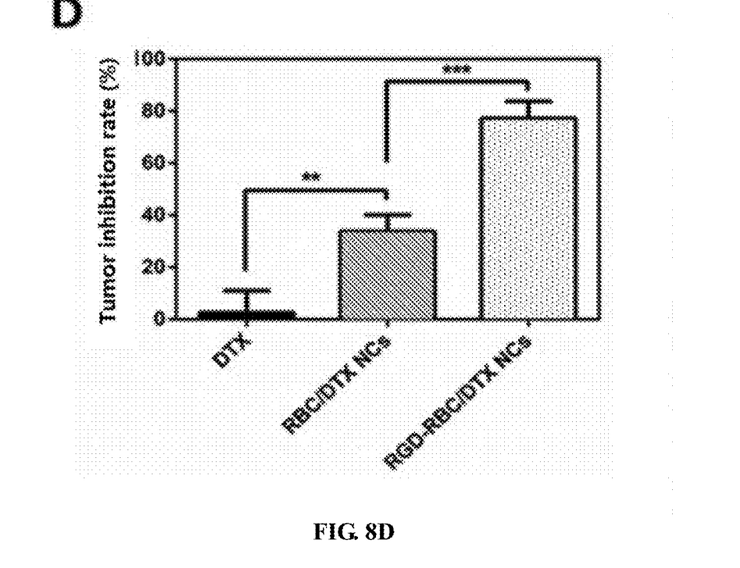
FIG. 8D is a comparison of tumor inhibition rates of various groups at a median survival time after administration. The results show that administrating with a docetaxel nanocrystal (DTX NCs) immediately causes model nude mice to die. While the docetaxel nanocrystals after being coated with erythrocyte membrane (RBC/DTX NCs) losses its toxicity, moreover, compared with normal saline (phosphate buffer saline (PBS)) (a median survival time is 27.5 days) and a commercially available docetaxel injection (DTX) (a median survival time is 38 days), the nano drug delivery system of the erythrocyte membrane-coated docetaxel nanocrystal (RBC,DTX NCs) significantly prolongs a survival time of model nude mice (a median survival time is 42 days). The nano drug delivery system of the RGD modified erythrocyte membrane-coated docetaxel nanocrystal (RGD-RBC/DTX NCs) prolongs the survival time of the model nude mice most significantly (a median survival time is 47 days). Tumor inhibition rates of the various groups on the 28$^{th}$ day after administration are respectively shown as follows: the tumor inhibition rate of the RBC/DTX NCs group is 89.18±6.75%, and the tumor inhibition rate of the RGD-RBC/DTX NCs group is 97.28±2.46%, which are significantly higher than that of the DTX group (53.28±19.79%). Tumor inhibition rates the various groups at the median survival time after administration are respectively shown as follows: the tumor inhibition rate of the RBC/DTX NCs group is 33.76%±6.37%, and the tumor inhibition rate of the RGD-RBC/DTX NCs group is 77.24%±6.58%, which are also significantly higher than that of the DTX group (4.93%±2.52%). The results show that the RGD-RBC/DTX NCs has the best anti-tumor effect in vivo.

In Vivo Pharmacodynamic Evaluations of Nano Drug Delivery System of Erythrocyte Membrane-Coated Docetaxel Nanocrystal and Nano Drug Delivery System of RGD Modified Erythrocyte Membrane-Coated Docetaxel Nanocrystal The U87 subcutaneous tumor animal models were constructed, and the tumor size was observed regularly. When the tumor size reached 150 mm³, the test was performed in groups. The groups were administered with PBS (pH 7.4), a commercially available docetaxel injection (DTX), a docetaxel nanocrystal (DTX NCs), the nano drug delivery system of the erythrocyte membrane-coated docetaxel nanocrystal (RBC,DTX NCs), and the nano drug delivery system of the RGD modified erythrocyte membrane-coated docetaxel nanocrystal (RGD-RBC/DTX NCs) by tail vein injections, respectively. The docetaxel was administered at a total dose of 25 mg/kg in a single dose. The survival time of the nude mice was recorded (FIG. 8A), and the large diameter (a) and small diameter (b) of the tumor were measured every other day. The tumor volume of each group of nude mice was calculated according to a formula, and the curve of tumor volume over time was plotted (FIG. 8B) and the tumor inhibition rate was calculated (FIGS. 8C and 8D). The tumor volume was calculated according to the following formula:

$$V_{tumor\ volume} = 0.5(a \times b^2)$$

Figure 9:
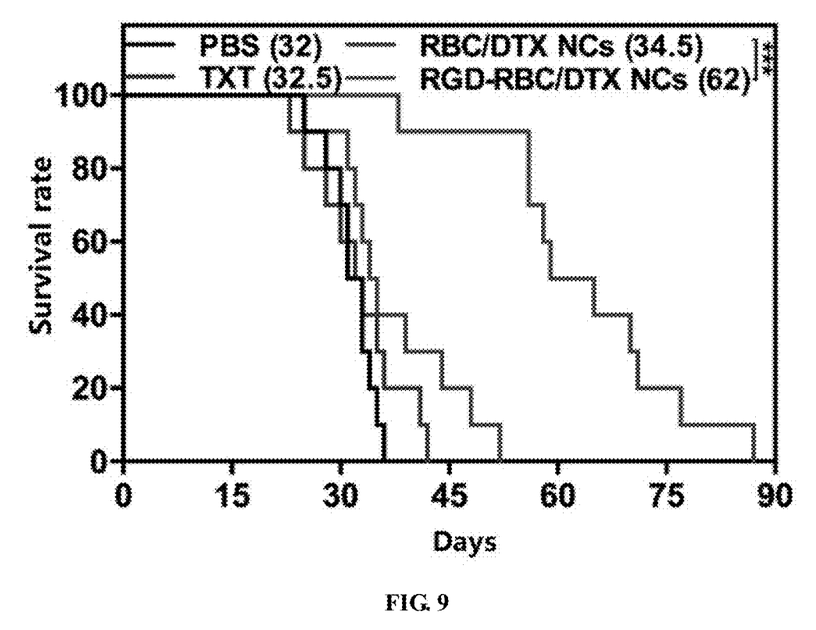
FIG. 9 shows anti-U87 intracerebral orthotopic tumor evaluations of a nano drug delivery system of an erythrocyte membrane-coated docetaxel nanocrystal and a nano drug delivery system of an RGD modified erythrocyte membrane-coated docetaxel nanocrystal: Survival curves of U87 intracerebral orthotopic tumor model nude mice are shown in the figure. The results show that, compared with normal saline (PBS) (a median survival time is 32 days), a commercially available docetaxel injection (DTX) (a median survival time is 32.5 days) and the nano drug delivery system of the erythrocyte membrane-coated docetaxel nanocrystal (RBC/DTX NCs) (a median survival time is 34.5 days), the nano drug delivery system of the RGD modified erythrocyte membrane-coated docetaxel nanocrystal (RGD-RBC/DTX NCs) significantly prolongs mouse survival time (a median survival time is 62 days).

The tumor inhibition rate was calculated to the following formula:

Tumor inhibition rate (%)=$(1 - V_{test\ group\ tumor\ volume} / V_{control\ group\ tumor\ volume}) \times 100$ The U87 orthotopic tumor animal models were constructed, and were administered with PBS (pH 7.4), a commercially available docetaxel injection (DTX), a docetaxel nanocrystal (DTX NCs), the nano drug delivery system of the erythrocyte membrane-coated docetaxel nanocrystal (RBC/DTX NCs), and the nano drug delivery system of the RGD modified erythrocyte membrane-coated docetaxel nanocrystal (RGD-RBC/DTX NCs) by tail vein injections 10 days after tumor implantation, respectively. The docetaxel was administered at a total dose of 25 mg/kg in a single dose. The survival time of the nude mice was recorded (FIG. 9).

Embodiment 8

Figure 10A:
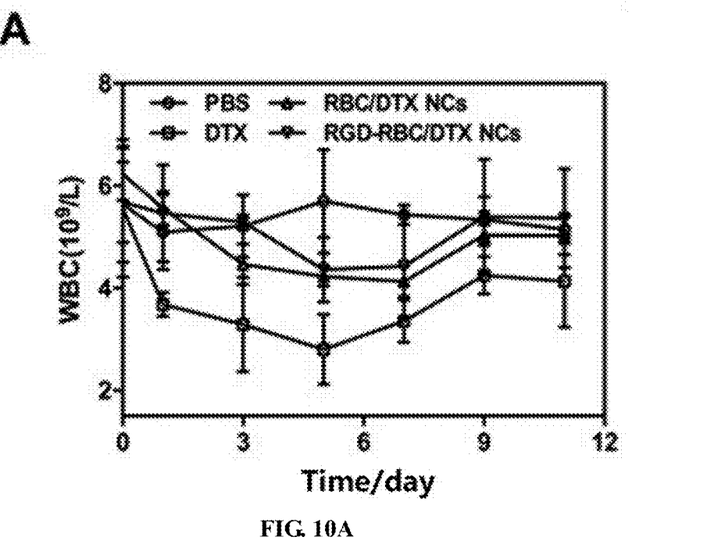
FIG. 10A shows a change in the number of white blood cells in whole blood within 12 days after administration in normal nude mice. The results show that a commercially available docetaxel injection (DTX) significantly reduces a level of white blood cells in mice, reaching a minimum value 5 days after administration, and returning to a normal level 10 days after the administration; and the nano drug delivery system of the erythrocyte membrane-coated docetaxel nanocrystal (RBC/DTX NCs) and the nano drug delivery system of the RGD modified erythrocyte membrane-coated docetaxel nanocrystal (RGD-RBC/DTX NCs) can significantly slow down the decrease of the number of the white blood cells.
Figure 10B:
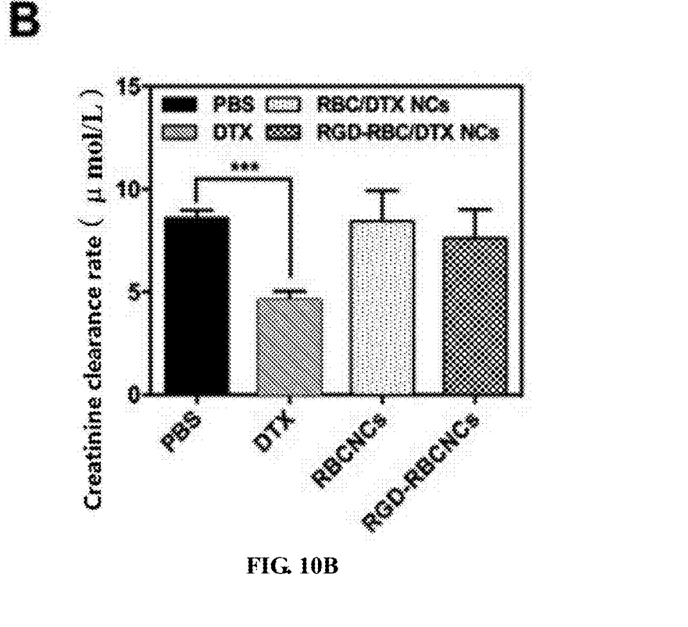
FIG. 10B shows a creatinine clearance rate 12 days after administration to normal nude mice. The results show that the DTX significantly reduces the creatinine clearance rate in mice and has nephrotoxicity, and the creatinine clearance rates of the RBC,DTX NCs, RGD-RBC/DTX NCs and normal saline groups are not distinctly different.

Safety Evaluations of Nano Drug Delivery System of Erythrocyte Membrane-Coated Docetaxel Nanocrystal and Nano Drug Delivery System of RGD Modified Erythrocyte Membrane-Coated Docetaxel Nanocrystal Normal nude mice were administered with normal saline, a commercially available docetaxel injection (DTX), the nano drug delivery system of the erythrocyte membrane-coated docetaxel nanocrystal (RBC,DTX NCs), and the nano drug delivery system of the RGD modified erythrocyte membrane-coated docetaxel nanocrystal (RGD-RBC/DTX NCs) by tail vein injections, respectively. The docetaxel was administered at a total dose of 25 mg/kg in a single dose. Whole blood was taken on days 1, 3, 5, 7, 9, and 11 after administration for measuring the number of leukocytes (FIG. 10A). The serum was taken on day 12 after administration to determine the creatinine clearance rate (FIG. 10B).

---

What is claimed is:

1. A nano drug delivery system, comprising a biofilm-coated drug nanocrystal, wherein the drug is in the physical form of a nanocrystal, and the drug nanocrystal is coated with a biofilm, wherein, a surface of the nano drug delivery system is further modified by a targeting molecule to construct the nano drug delivery system as a nano drug delivery system of a biofilm-coated nanocrystal with an active targeting capability;

the targeting molecule is a polypeptide targeting molecule; and the polypeptide targeting molecule is one or more selected the group consisting of RGD, VAP, WVAP, A7R, and CDX;

wherein, the drug is at least one selected from the group consisting of a therapeutic drug and a diagnostic agent;

wherein, the therapeutic drug is one or more selected from the group consisting of: an anti-tumor drug, an anti-infective drug, an anti-cardiovascular disease drug, an anti-lymphatic system disorder drug, an anti-immune system disorder drug, and an analgesic drug, and the therapeutic drug is in the physical form of the nanocrystal;

wherein, the anti-tumor drug is one selected from the group consisting of: a taxane drug, an anthracycline drug, a camptothecin drug, a vincristine drug, and a zomib drug, irinotecan and a parthenolide drug; the anti-infective drug is one selected from the group consisting of ceftriaxone, cefoxitin, aztreonam, streptomycin, amphotericin B, vancomycin, tigecycline, teicoplanin, moroxydine, vidarabine and acyclovir; the anti-cardiovascular disease drug is one selected from the group consisting of ganglioside, ferulic acid, ligustrazine, troxerutin, and sodium ozagrel the anti-lymphatic system disorder drug is panobinostat; the anti-immune system disorder drug is one selected from the group consisting of methylprednisolone and cyclosporine; and the analgesic drug is one selected from the group consisting of morphine and methadone;

wherein, the diagnostic agent is a fluorescent substance and is in the physical form of the nanocrystal; and wherein, the biofilm has a membrane structure with a lipid bilayer, and the biofilm is a natural cell membrane; wherein the natural cell membrane is one or more selected from the group consisting off an erythrocyte membrane, a platelet membrane, a macrophage membrane, a leukocyte membrane, and a tumor cell membrane.

2. The nano drug delivery system of claim 1, wherein, the drug nanocrystal has a particle size of 10-1000 nm.

3. A method comprising administering the nano drug delivery system of claim 1 to a subject in need thereof.

* * * * *